(12) United States Patent
Herczegh et al.

(10) Patent No.: US 6,333,424 B1
(45) Date of Patent: Dec. 25, 2001

(54) THERAPEUTIC DERIVATIVES OF DIPHOSPHONATES

(75) Inventors: Pal Herczegh, Debrecen (HU); John F. Hartmann, Princeton Junction, NJ (US); Arpad Kovacs, Miskolo (HU); Ferenc J. Sztaricskai; Miklos Hornyak, both of Debrecen (HU)

(73) Assignee: Eliza Nor Biopharmaceuticals, Inc., Princeton Junction, NJ (US)

( * ) Notice: Subject to any disclaimer, the term of this patent is extended or adjusted under 35 U.S.C. 154(b) by 0 days.

(21) Appl. No.: 09/269,974

(22) PCT Filed: Oct. 9, 1997

(86) PCT No.: PCT/US97/18270

§ 371 Date: Apr. 8, 1999

§ 102(e) Date: Apr. 8, 1999

(87) PCT Pub. No.: WO98/15560

PCT Pub. Date: Apr. 16, 1998

Related U.S. Application Data

(60) Provisional application No. 60/027,990, filed on Oct. 9, 1996.

(51) Int. Cl.[7] .............................. C07F 9/02; C07F 9/28; C07F 9/38; C07F 9/44; C07C 29/04

(52) U.S. Cl. ..................... 558/159; 514/121; 558/160; 544/337

(58) Field of Search ................................ 558/159, 160; 544/337

(56) References Cited

PUBLICATIONS

STN International, CAPLUS Database, Chemical Abstracts Service, (Columbus, Ohio), No. 1996:242762; Wu, Y. et al. Zhongguo Yaowu Huaxue Zazhi 1995, 5(4), pp. 254–257, abstract.*

* cited by examiner

*Primary Examiner*—Floyd D. Higel
*Assistant Examiner*—Benjamin Sackey
(74) *Attorney, Agent, or Firm*—D. J. Perrella

(57) ABSTRACT

Compounds having utility in achieving the foregoing objects of the invention are prepared by reacting a 2,2-bis-(disubstituted-phosphoryl)-ethylsulfanyl-acetic acid compound with a pharmaceutically active chemical entity effective to treat the underlying disease state or with non-pharmaceutical entities such as pesticides, insecticides, fungicides or poisons for vermin.

13 Claims, No Drawings

THERAPEUTIC DERIVATIVES OF DIPHOSPHONATES

This application is a 371 of PCT/US97/18270 filed Oct. 9, 1997 which claims benefit of U.S. Provisional Application Ser. No. 60/027,990, filed Oct. 9, 1996.

BACKGROUND OF THE INVENTION

WO 96/40156 and WO 96/40190, each published Dec. 19, 1996, disclose therapeutic derivatives of diphosphonates. These compounds have the formula A—V' and are obtained by reacting a diphosphonic acid compound with a pharmaceuticaly active entity. In these compounds of formula A—V', A is the residue of a pharmaceutically active entity and V' is the residue of the diphosphonic acid compound.

OBJECTS OF THE INVENTION

It is an object of the present invention to provide novel pharmaceutically active compounds having improved utility for treating various diseases, especially diseases of the bones and teeth, Further objects are to provide new pharmaceutically active chemical entities for treating infectious diseases of bone and teeth, osteomyelitis, periodontal disease, urinary catheter-related infections, infectious urinary calculi, gastritis and peptic ulcers, and bone cancer. Another object is to provide intermediates for preparing these new chemical entities. Still another object is to provide methods for treating these diseases, and methods for preparing the pharmaceutically active agents. These and other objects of the present invention will be apparent from the following description.

SUMMARY OF THE INVENTION

Therapeutic agents having utility in achieving the foregoing objects of the invention are obtained with compounds prepared by reacting a 2,2-bis-(disubstituted-phosphoryl)-ethylsulfanyl-acetic acid compound with a pharmaceutically active chemical entity effective to treat the underlying disease.

DETAILED DESCRIPTION

The pharmaceutically active therapeutic agents of the present invention are compounds obtained by reacting a 2,2-bis-(disubstituted-phosphoryl)-ethylsulfanyl-acetic acid compound with a pharmaceutically active chemical entity effective to treat the underlying disease, i.e., an infectious disease of bone or teeth, osteomyelitis, periodontal disease, urinary catheter-related infections, infectious urinary calculi, gastritis and peptic ulcers, and bone cancer. The diphosphonate moiety causes the therapeutic agent to be attracted to, and to concentrate on, the surfaces of various salt crystals and the more complex forms of such crystals, such as hydroxyapatite, a major constituent of bone and the surface of dentition. Bacteria associated with these crystals are thereby exposed to an elevated concentration of the therapeutic agent, relative to the surrounding milieu. The therapeutic moiety is derived from a pharmaceutical that is pre-selected because of its recognized ability to treat the underlying disease state. The diphosphonate intermediates of the present invention can be prepared by reacting thioglycolic acid with a tetraester of ethylidene-diphosphonic acid, $H_2C = C(PO_3R_2)_2$, wherein the group R is an alkyl group of 1–10 carbons. The reaction product is the corresponding 2,2-bis-(di-substituted-phosphoryl)-ethylsulfanyl-acetic acid compound. The latter compound is then reacted with a pharmaceutically active compound of the formula A—NH$_2$ or A—COOCH$_2$Cl wherein A is the residue of the pharmaceutically active compound, that is to say, it is the pharmaceutically active compound less the H or Cl atom lost in the coupling reaction with the 2,2-bis-(di-substituted-phosphoryl)-ethylsulfanyl-acetic acid compound. (If neither of the —NH$_2$ or —COOCH$_2$Cl groups are present in the pharmaceutically active compound, they are introduced by using conventional chemical techniques known to those skilled in organic and medicinal chemistry fields). In the former case the resulting compound has the following formula

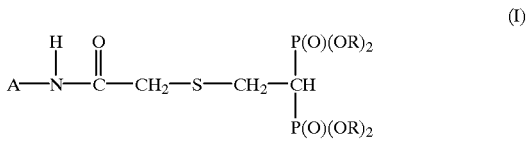

(I)

while in the latter case the chloro compound is replaced by the group

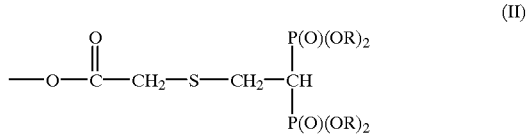

(II)

whereby the resulting compound has the formula

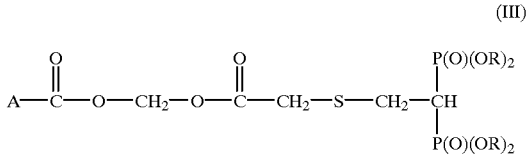

(III)

The above-illustrated compound is susceptible to in vivo and in vitro cleavage by the enzyme esterase whereby the starting pharmaceutically active compound is reconstituted.

Other compounds of the present invention are illustrated by the formula A—X—Z wherein A is the residue of a pharmaceutically active compound, X is a linking group that is cleavable in vivo and in vitro by an endogenous enzyme, and Z is

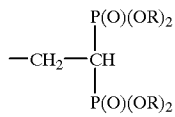

wherein R is H or alkyl of from 1 to 10 carbons. An example of such an endogenous enzyme is esterase, in which case of esterase the cleavable group has the structural formula

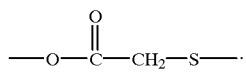

The reaction between the pharmaceutically active compound and the 2,2-bis-(di-substituted-phosphoryl)-ethylsulfanyl-acetic acid compound takes place under well-known conventional and standard conditions for reactions of this type. An illustration of these reaction conditions is shown in Example 2. Additional illustrations are shown in the two published disclosures mentioned above, WO 96/40156 and WO 96/40190.

The 2,2-bis-(di-substituted-phosphoryl)-ethylsulfanyl-acetic acid compounds of the present invention are prepared by reacting thioglycolic acid with a tetra-substituted ethylidene diphosphonate compound wherein the alkyl group has from 1 to 10 carbon atoms. The reaction preferably takes place in a polar solvent, such as a halogenated hydrocarbon, e.g., dichloromethane, for a period of from about 1 or 2 hours to about 20 hours at a temperature of from about 10° C. to about 30° C. Compounds wherein R is H are obtained by reacting any of the foregoing compounds wherein R is alkyl with bromotrimethyl silane, then with water. The reaction is preferably carried out in a polar solvent, preferably dry, such as a halogenated hydrocarbon, a specific example of which is dichloromethane, at about room temperature followed by addition of water.

Compounds of the present invention have been shown to bind in a saturable way to a slurry of rat tibia and to show activity against microorganisms. Other tests have shown that the binding increases with time and that the bound compound can be removed from the bone slurry by exposure to $CaCl_2$. Taken together these tests demonstrate that the compounds of the present invention bind to and are retained by calcium sites in bone and, further, inactivate bacteria.

The compounds of the present invention are intended for treatment of a member of a mammalian species, e.g., dogs, mice, primates and humans, and normally are administered orally but also can be administered by other routes, for example, parenterally or by injection. In general, these compounds can be used at a dosage amount that is in the range of from about 10% to about 1000%, preferably from about 25% to about 750%, and most preferably from about 50% to about 500% that at which the pharmaceutically active component itself is used. The compounds of the present invention are used in the form of various pharmaceutical preparations such as tablets, capsules, granules, syrups and the like which are well known in the art, and which can be prepared by methods known per se using suitable diiuents, bindings, disintegrators, coating agents and the like. Other preparations suitable for injection or parenteral use also can be prepared by techniques known in the art.

Other non-pharmaceutical compounds are obtained in similar manner by replacing the pharmaceutically active compound with an insecticide, fungicide, poison for vermin, and the like.

Examples of useful pharmaceutically active chemical entities suitable for reaction with the 2,2-bis-(di-substituted-phosphoryl)-ethylsulfamyl-acetic acid compounds of the present invention include, without intending to be limited thereby:

an aminoglycoside such as amikacin (U.S. Pat. No. 3,781,268), ampramycin (U.S. Pat. No. 3,691,279), arbekacin (U.S. Pat. No. 4,107,424), bambermycin (U.S. Pat. No. 3,674,866), butirosin (U.S. Pat. No. 3,541,078), dibekacin (German patent 2,135,191), dihydrostreptomycin (U.S. Pat. No. 2,498,574), fortimycin A (U.S. Pat. No. 3,976,768) and fortimycin B (Japan Kokai 75 145,588), gentamicin (U.S. Pat. Nos. 3,091,572 and 3,136,704), isepamicin (Belgian patent 818,431), kanamycin (U.S. Pat. No. 2,931,798), micronomicin (German patent 2,326,781), neomycin (2,799,620), neomycin undecylenate (U.S. Pat. No. 3,022,286), netilmicin (German patent 2,437,160), paromomycin (U.S. Pat. No. 2,916,485), ribostamycin (German patent 1,814,735), sisomicin (U.S. Pat. No. 3,832,286), spectinomycin (U.S. Pat. No. 3,234,092), streptomycin (U.S. Pat. No. 2,868,779), streptonicozid (Pennington et al., J. Am. Chem. Soc. 75, 2261 (1953) and tobramycin (Stark et al., Higgens, Kastner, Thompson, Presti, Wick, Welles, Antimicrob. Ag. Chemother., 1967, 314–348;

an amphenicol such as azidamfenicol (U.S. Pat. No. 2,882,275), chloramphenicol [Bartz, J. Biol. Chem. 172, 445 (1948)], chloramphenicol palmitate (U.S. Pat. No. 2,662,906), chloramphenicol pantothenate (U.S. Pat. No. 3,078,300), florfenicol (U.S. Pat. No. 4,235,992) and thiamphenicol (Cutler et al., J. Am. Chem. Soc. 74, 5475 (1952)];

an ansamycin such as rifamide (U.S. Pat. No. 3,313,804); carbapenem, for example, imipenem (U.S. Pat. No. 4,194,047); cephalosporin, for example, cefaclor (U.S. Pat. No. 3,925,372), cephadroxil U.S. Pat. No. 3,816,253), cefamandole U.S. Pat. No. 3,641,021), cefatrizine (U.S. Pat. No. 3,970,651), cefazedone (German patent 2,345,4,02), cefazolin (U.S. Pat. No. 3,516,997), cefixime (U.S. Pat. No. 4,409,214), cefmenoxime (U.S. Pat. No. 4,098,888), cefodizime (U.S. Pat. No. 4,278,793), cefonicid (U.S. Pat. No. 4,093,723), cefoperazone (U.S. Pat. No. 4,410,5220, ceforanide (U.S. Pat. No. 4,172,196), cefotaxime (U.S. Pat. No. 4,098,888), cefotiam (German patent 2,607,064), cefpimizole (U.S. Pat. No. 4,217,450), cefpiramide (Belgian patent 833,063), cefpodoxime proxetil (U.S. Pat. No. 4,486,425), cefroxidine (U.S. Pat. No. 4,073,902), cefsulidin, (U.S. Pat. No. 4,065,619), ceftazidime (U.S. Pat. No. 4,258,041), cefteram (Belgian patent 890,499), ceftozole (U.S. Pat. No. 3,516,997), ceftibuten (U.S. Pat. No. 4,634,697), ceftizoxime (U.S. Pat. No. 4,427,674), ceftriaxone (U.S. Pat. No. 4,327,210), cefuroxime (U.S. Pat. No. 3,974,153), cefuzonam (U.S. Pat. No. 4,399,132), cephalexin (U.S. Pat. No. 3,275,626), cephaloglycin (U.S. Pat. No. 3,422,103), cephaloridine (French patent 1,364,197), cephalosporin C (U.S. Pat. No. 3,082,155), cephalothin (French patent 1,384,197), cephapirin sodium (U.S. Pat. No. 3,422,100), cephradine (U.S. Pat. No. 3,485,819) and pivecfalexin (German patent 1,951,012);

a cephamycin such as cefbuperazone (U.S. Pat. No. 4,263,292), cefmetazole (U.S. Pat. No. 4,007,177), cefminox (U.S. Pat. No. 4,357,331), cefotetan (U.S. Pat. No. 4,263,432) and cefoxitin (U.S. Pat. No. 4,297,488);

a monobactam such as aztreonam (Netherlands patent application 8,100,571, carumonam (U.S. Pat. No. 4,572,801), and tigemonam (U.S. Pat. No. 4,638,061);

an oxacephem such as flomoxef (U.S. Pat. No. 4,532,233) and moxalactam (U.S. Pat. No. 4,138,486);

a penicillin such as amdinocillin (U.S. Pat. No. 3,957,764, amoxicillin (U.S. Pat. No. 3,192,198) ampicillin (U.S. Pat. No. 2,985,648), carbenicillin (U.S. Pat. No. 3,142,673), clometocillin (U.S. Pat. No. 3,007,920), cloxacillin (Doyle et al., J. Chem. Soc. 1963, 5838), cyclacillin (U.S. Pat. No. 3,194,802), dicloxacillin (U.S. Pat. No. 3,239,507), epicillin (U.S. Pat. No. 3,485,819), floxacillin (U.S. Pat. No. 3,239,507), hetacillin (U.S. Pat. No. 3,198,804), lenampicillin (U.S. Pat. No. 4,342,693), metampicillin (Belgian patent 661,232), oxacillin (U.S. Pat. No. 2,996,501), penicillin V (Brandl et al., Wien. Med. Wochenschr. 1953, 602), piperacillin (U.S. Pat. No. 4,087,424), pivampicillin ((U.S. Pat. No.

3.660,575), propicillin (British patent 877,120), sulbenicillin (U.S. Pat. No. 3,660,379) and ticarcillin (U.S. Pat. No. 3,282,926);

a lincosamide such as clindamycin (U.S. Pat. No. 3,475,407) and lincomycin (U.S. Pat. Nos. 3,086,912 and 3,155,580); a macrolide such as azithromycin (U.S. Pat. No. 4,517,359), carbomycin (U.S. Pat. No. 2,960,438), clarithromycin (U.S. Pat. No. 4,331,803), erythromycin (U.S. Pat. No. 2,823,203), josamycin (Japanese patent 66 21 759), leucomycins (U.S. Pat. No. 3,535,309), midecamycins (U.S. Pat. No. 3,761,588), miokamycin (Japanese Kokai 74 124087), oleandomycin (U.S. Pat. Nos. 2,757,123 and 2,842,481), primy6in (U.S. Pat. No. 3,498,884), rokitamycin (German patent 2,918,954), rosaramicin (S. African patent 71 00,402), roxithromycin (U.S. Pat. No. 4,359,545), spiramycin (U.S. Pat. No. 2,943,023), and troleandomycin (British patent 877,730);

polypeptide such as bacitracin (U.S. Pat. No. 2,915,432), capreomycin (U.S. Pat. No. 3,143,468), colistin (Japanese patent 57 4898), enduracidin (British patent 1,163,270), enviomycin (U.S. Pat. No. 3,892,732), gramicidin (U.S. Pat. No. 2,534,541), mikamycin (French patent 1,349,946), polymyxin (U.S. Pat. No. 2,565,057), polymyxin B-methanesulfonic acid (U.S. Pat. No. 3,044,934), pristinamycin (U.S. Pat. No. 3,154,475), ristocetin (U.S. Pat. No. 2,990,329), teicoplanin (U.S. Pat. No. 4,239,751), thiostrepton (U.S. Pat. Nos. 2,982,689 and 2,982,698), tuberactinomycin (U.S. Pat. No. 3,639,580), tyrocidine (U.S. Pat. No. 3,265,572), tyrothricin, vancomycin (U.S. Pat. No. 3,067,099), viomycin (U.S. Pat. No. 2,633,445), virginiamycin, and zinc bacitracin (U.S. Pat. No. 2,803,584);

a tetracycline such as apicycline (Netherlands patent application 6,515,688), chlortetracycline (U.S. Pat. No. 2,482,055), clomocycline (Belgian patent 628,142), demeclocycline (U.S. Pat. No. 2,878,289), doxycycline (U.S. Pat. No. 3,220,149), guamecycline (British patent 1,042,207), lymecycline (U.S. Pat. No. 3,043,716), meclocycline 2,984,686), methacycline (U.S. Pat. No. 3,026,354), minocycline (U.S. Pat. Nos. 3,148,212 and 3,226,436), oxytetracycline (U.S. Pat. No. 2,516,080), penimepicycline (British patent 897,826), pipacycline (British patent 888,968), rolitetracycline (U.S. Pat. No. 3,104,240), sancycline (U.S. Pat. No. 3,019,260), senociclin (U.S. Pat. No. 3,218,335), and tetracycline (U.S. Pat. No. 2,699,054);

cycloserine (U.S. Pat. No. 2,733,878), doxorubicin (U.S. Pat. No. 3,590,028), and mupirocin (U.S. Pat. No. 3,977,943);

a 2,4-diaminopyrimidine such as bradimoprim (U.S. Pat. No. 4,024,145), tetroxoprim (U.S. Pat. No. 3,992,379), and trimethoprim (U.S. Pat. No. 3,049,544);

a nitrofuran such as furazolium chloride (U.S. Pat. No. 3,169,970), nifuradene (U.S. Pat. No. 2,746,960), nifurprazine (British patent 966,832), nifurtoinol (U.S. Pat. No. 3,446,802), and nitrofurantoin (U.S. Pat. No. 2,610,181);

a quinoline or quinolone analogs such as amifloxacin (U.S. Pat. No. 4,499,091), cinoxacin (U.S. Pat. No. 3,669,965), ciprofloxacin (U.S. Pat. No. 4,670,444), difloxacin (U.S. Pat. No. 4,730,000), enoxacin (U.S. Pat. No. 4,359,578), fleroxacin (U.S. Pat. No. 4,398,029), flumequine (U.S. Pat. No. 3,896,131), lomefloxacin (U.S. Pat. No. 4,528,287), miloxacin (U.S. Pat. No. 3,799,930), nalidixic acid (U.S. Pat. No. 3,149,104), norfloxacin (U.S. Pat. No. 4,146,719), ofloxacin (U.S. Pat. No. 4,382,892), oxclinic acid (U.S. Pat. No. 3,287,458), perfloxacin (U.S. Pat. No. 4,292,317), pipemidic acid (U.S. Pat. No. 3,887,557), piromidic acid (British patent 1,129,358), rosoxacin (U.S. Pat. No. 3,753,993), sparfloxacin (*Antimicrobial Agents & Chemotherapy*) 1989, 33, 1167–1173) and tosufloxacin (U.S. Pat. No. 4,704,459);

a sulfonamide such as acetyl sultamethoxypyrazine (U.S. Pat. No. 3,098,069), acetyl sulfisoxazole (U.S. Pat. No. 2,721,200), azosulfamide (U.S. Pat. Nos. 2,123,634 and 2,148,910), benzylsulfamide, chloramine-B, chloramine-T, dichloramine T (U.S. Pat. No. 2,495,489), formosulfathizale [Druey et al., *Helv. Chim. Acta* 31, 2184 (1948)), $N^2$-formylsulfisomidine (German patents 1,122,511 and 1,126,857), $N_4$-β-D-glucosyl-sulfanilamide [Kuhn et al., Ber. 71, 621 (1938)), mafenide (U.S. Pat. No. 2,288,531), 41-methylsulfamoyl)-sulfanilanilide (French patent 817,034), p-nitrosulfathiazole (U.S. Pat. No. 2,443,742), norprylsulfamide (U.S. Pat. No. 2,262,544), phthalylsulfacetamide [(Basu, *J. Indian Chem. Soc.* 26, 130 (1949)), phthalylsulfathiazole (U.S. Pat. Nos. 2,324,013 and 2,324,015), salazosulfadimidine [Korkuczanski, *Przem. Chem.* 37, 162 (1958)), succinylsulfathiazole (U.S. Pat. Nos. 2,324,013 and 2,324,014), sulfabenzamide (U.S. Pat. No. 2,240,496), sulfacetamide (U.S. Pat. No. 2,411,495, sulfachlorpyridazine (U.S. Pat. No. 2,790,798), sulfachrysoidine [Gley et al., *Compt. Rend. Soc. Biol.* 125, 1027 (1937)), sulfacytine (U.S. Pat. No. 3,375,247), sulfadiazine (U.S. Pat. No. 2,407,966), sulfadicramide (U.S. Pat. No. 2,417,005), sulfadimethoxine (U.S. Pat. No. 2,703,800), sulfadoxine (U.S. Pat. No. 3,132,139), sulfaethidole [Wojahn et al., *Arch. Pharm.*, 284, 53 (1951)], sulfaquanidine (U.S. Pat. Nos. 2,218,490, 2,229,784 and 2,233,569), sulfaguanole (U.S. Pat. No. 3,562,258), sulfalene (U.S. Pat. No. 3,098,069), sulfaloxic acid (German patent 960,190), sulfamerazine (U.S. Pat. No. 2,407,966), sulfameter (U.S. Pat. No. 3,214,335), sulfamethazine (U.S. Pat. No. 2,407,966), sulfamethizole (U.S. Pat. No. 2,447,702), sulfamethomidine (German patent 926,131), sulfamethoxazole (U.S. Pat. No. 2,888,455), sulfamethoxypyridazine (U.S. Pat. No. 2,712,012), sulfametrole (U.S. Pat. No. 3,247,193), and sulfamidochrysoidine (U.S. Pat. No. 2,085,037);

a sulfone such as acedapsone [Fromm et al., Ber, 41, 2270 (1908)], acediasulfone [Jackson, *J. Am. Chem. Soc.* 70, 680 (1948)], acetosul-fone sodium (U.S. Pat. No. 2,358,365), dapsone (French patent 829,926), diathymosulfone (British patent 758,744), glucosulfone sodium (Swiss patent 234,108), solasulfone (British patent 491,265), succisulfone (U.S. Pat. No. 2,268,754), sulfonilic acid, p-sulfanilyl-benzylamine (Dewing, *J. Chem. Soc*, 1946, 466), p,p'-sulfonyl-dianiline-N,N1-digalactoside, sulfoxone sodium (U.S. Pat. No. 2,256,575), and thiazolsulfone (2,389,126);

others such as clofoctol (U.S. Pat. No. 3,820,852), hexedine (U.S. Pat. No. 3,357,886), nitroxoline [Kostanecki, *Ber.* 24, 154 1891)1, xibornol (British patent 1,206,774; hydnocarpic acid [Diaper et al., *Biochem J*. 42, 581 (1948)], p-aminosalicylic acid (U.S. Pat. No. 427,564), p-aminosalicylic acid hydrazide (Spanish patent 206,645), benzoylpas (British patent 676,363), 5-bromosalicylhydroxamic acid (Urbanski et al., *Nature,* 170, 753 (1952), capreomycin (U.S. Pat. No. 3,143,468), clofazimine (Barry et al., *Nature* 179, 1013 (1957), cyacetacide (U.S. Pat. No. 2,849,369), dihydrostreptomycin (U.S. Pat. No. 2,498, 574), enviamycin (U.S. Pat. No. 3,892,732), ethambutol [Wilkinson et al., *J. Am. Chem. Soc.* 83, 2212 (1961)), ethionamide (British patent 800,250), 4'-formylsuccinanilic acid (German patent 852,086), furonazide [Miyatake et al. *J. Pharm. Soc. Japan* 75, 1066, (1955)], glyconiazide (U.S. Pat. No. 2,940,899), isobutol (U.S. Pat. No. 3,718,655), isonizid (U.S. Pat. No. 2,830,994), isoniazid methanesuifonate (U.S. Pat. No. 2,759,944), morphazinzmide (German patent 1,129,492), opiniazide [Pershin et al., C.A. 51, 10747e (1957)], pasiniazide (Swiss patent 303,085), phenyl aminosalicylate (U.S. Pat. No. 2,604,488), protionamide (British patent (800,250), pyrazinamide (German patent (632,257), rifampin (U.S. Pat. No. 3,342,810), salinizid [Hart et al., *Antibot. & Chemother.* 4, 803 (1954)], subathizone [Bernstein et al., *J. Am. Chem. Soc.* 73, 906 (1951), sulfoniazide (U.S. Pat. No. 2,727, 041), thiacetazone [Domagk et al., *Naturwiss* 33, 315 (1946)), tiocarlide (U.S. Pat. No. 2,703,815), tuberactinomycin (U.S. Pat. No. 3,639,580), tuberculin [Anzai et al., *J. Antiobiot.* 10A, 201 (1957)], tuberin (Japanese patent 64 7399), verazide [Fox et el., *J. Org. Chem.* 18, 983 (1953), viomycin (U.S. Pat. No. 2,633,445), and viomycin pantothenate (German patents 954,874 and 1,011,800).

EXAMPLE 1

A. 2,2-Bis-(diethoxyphosphoryl)-ethylsullfanyl-acetic acid

Tetraethyl ethylidenephosphonate (3.6 g, 12 mmol) was dissolved in dry dichloromethane (30 ml), thioglycolic acid (1.1 g, 12 mmol) was added and the mixture was allowed to react overnight. It was evaporated and the residue was purified using column chromatography using a dichloromethane-methanol 9:1 mixture as eluant to give 4.5 g 5.7%) of the title compound as a syrup. MS m\e 392 (M). $^1$H-NMR: $\delta$4.20 (8H, q, OCH$_2$); (2H, s, SCH$_2$COOH); 3.20 (2H, m, CH$_2$); 2.8 (1H, m, —CH—); 1.35 (12H, t, —CH$_3$).

B. 7-(4-((2,2-Bis-(diethoxyphosphoryl)-ethylsulfanyl)-acetoxymethoxycarbonyl)-piperazin-1-yl)-1-ethyl-6-fluoro-4-oxo-1,4-dihydroquinoline-3-carboxylic acid A solution of 1-ethyl-6-fluoro-1,4-dihydro-4-oxo-7-[4'-[(1"-chlIoroethoxy) carbonyl]-1'-piperazinyl]-quinoline-3-carboxylic acid (*J. Med. Chem.* 34, 78 (1991) (0.8 g, 1.9 mmol), 2,2-bis-(diethoxyphosphoryl)-ethylsulfanyl-acetic acid (1 g, 5 mmol) and triethylamine (0.37 ml, 2.6 mmol) in dry dimethylformamide (14 ml) was stirred at 90° C. for 2 hours. After evaporation of the solvent the residue was extracted with dichloromethane. The solvent was distilled off and the residue was purified by column chromatography using dichloromethane-methanol 98:2, then 97:3 and 95:5 mixtures as eluants to yield 0.15 g (10%) of the title compound. M.p.: 89–90° C. MS (FAB) m/e 768 (M+1). $^1$H-NMR $\delta$ (CDCl$_3$) 15.0 (1H, s, —COOH); 8.68 (10H, s, H-2); 8.05 (1H, d, H-5) 6.9 (1H, d, H-8), 5,85 (2H, s, 2"-CH$_2$); 4.2 (4H, m, OCH$_2$) 3.8 (4H, m, 3'-CH2+5-CH$_2$); 3.4 (2H, s, 4"-CH$_2$); 3.1–3.3 (6H, m, 2'-CH$_2$, +5'-CH$_2$); 2.7 (1H, m, 6"-CH); 1.6 (3H, t, NCH$_2$CH$_3$,); 1.4 (12H, t, OEt). $^{13}$C-NMR (CDCl$_3$) $\delta$ 177.2; 169.6; 167.3; 155.2; 153.5; 152.4; 147.5; 146.1; 146.0; 121.4; 1 mmol) and 2,6-dimethylpyridine (0.11 ml, 1 mmol) in dry tetrahydrofuran (5 ml). The mixture was held at −10° C. for 15 minutes to complete formation of the mixed isobutoxyformic anhydride. An ice-cold solution of amoxicillin (0.42 g, 1 mmol) and 2,6-dimethylpyridine (0.17 ml, 1.5 mmol) in a 1:1 mixture of tetrahydrofurane and water (6 ml) was acided rapidly, and the mixture was stirred at 0° C. to 5° C. for 1 hour and then for a further 1 hour while it attained room temperature. Tetrahydrofurane was removed under reduced pressure, then the residue was dissolved in 20 ml water. The slightly basic (pH=7.5) aqueous solution was extracted with ethyl acetate (3×15 ml), and the organic phase was set aside. The aqueous phase was cooled to 0° C., acidified to pH=2.5 with 0.1 M HCl, and extracted with ethyl acetate (3×30 ml). The organic phase was dried over MgSO$_4$ and the solvent evaporated to give 0.35 (48%) crystalline product., m.p.: 104–106° C.

Anal.: Calc'd. for $C_{28}H_{43}N_3O_{12}P_2S$: C, 45.46; H, 5.86, N, 5.68; P, 8.37

Found: I C, 45.80; H, 6.18; N, 5.66; P, 8.20

IR: 1786 cm$^{-1}$ ($\beta$-lactame C=O)

FAB_MS: 739 (M+)

0H-NMR (200 MHz, in DMSO): $\delta$: 5.7 (dd, 1H, H-6), 5.4 (d, IH, H-6); 5.4 (d, 1H, H-5); 4. (m, 8H, P(0)CH$_2$CH$_3$); 1.2 (m, 12H, P(O)CH$_2$CH$_3$).

EXAMPLE 3

2,2-Bis-(dimethoxyphosphoryl)-methyl sulfany-acetic acid

Following the procedure of Example 1 A but substituting for tetraethyl ethylidenephosphonate an equivalent amount of tetramethyl ethylidenephosphonate, the title compound is obtained.

EXAMPLE 4

2,2-Bis-(dipropoxyphosphoryl)-n-propylsulfanyl-acetic acid

Following the procedure of Example 1 A but substituting for tetraethyl ethylidene phosphonate an equivalent amount of tetra-n-propylethylidene phosphonate, the title compound is obtained.

EXAMPLE 5

The MIC values ($\mu$g/ml) of the compound of Example 1 B and of norfloxacin were determined against various organisms by the agar dilution method with the following results.

| Bacteria | Norfloxacin MIC = $\mu$g/ml | Compound of Example 1 B MIC = $\mu$g/ml |
|---|---|---|
| *Staphylococcus aureus* ATCC 25923 | 6.25 | 6.25 |
| *Staphylococcus epidermis* OKI 110001 | 1.56 | 1.56 |
| *Streptococcus fecalis* OKI 80171 | 12.5 | 12.5 |
| *Salmonella typhi* OKI 10084 | $\geq$0.39 | $\geq$0.78 |
| *Escherichia coli* OKI 35034 | $\geq$0.39 | 0 $\geq$0.39 |
| *Proteus vulgaris* OKI 60002 | 0.78 | 1.56 |
| *Pseudomonas aeruginosa* ATCC 27853 | 12.5 | 12.5 |
| *Helicobacter pylori* 27604 | 6.25 | 6.25 |
| *Helicobacter pylori* 27606 | 6.25 | 3.12 |

EXAMPLE 6

The MIC values (μg/ml) of the compound of Example 2 and of amoxicillin were determined against various organisms by the agar dilution method with the following results.

| Bacteria | Amoxicillin MIC = μg/ml | Compound of Example 2 MIC = μg/ml |
|---|---|---|
| *Staphylococcus aureus* ATCC 25923 | ≧0.39, 0.78 | 6.25, 6.25 |
| *Staphylococcus epidermis* OKI 110001 | ≧0.39, ≧0.39 | 6.25, 12.5 |
| *Streptococcus fecalis* OKI 80171 | 1.56, ≧0.39 | 25, >12.5 |
| *Salmonella typhi* OKI 10084 | 0.78, 3.12 | 25, >50 |
| *Escherichia coli* OKI 35034 | 25, 50 | >100, 100 |
| *Proteus vulgaris* OKI 60002 | 50, 100 | >100, 100 |
| *Pseudomonas aeruginosa* ATCC 27853 | >100, >100 | >100, >100 |
| *Helicobacter pylori* 27604 | ≧0.39 | ≧0.39 |
| *Helicobacter pylori* 27606 | ≧0.39 | ≧0.78 |

EXAMPLE 7

7-(4-(2,2-Bis-phosphonoethyl-piperazin-1-yl-ethyl-6-fluoro-4-oxo-1,4-dihydroquinoline-3-carboxylic acid To a solution of 7-(4-(2,2-bis-diethoxy-phosphoryl)-ethyl-6-fluoro-4-oxo-1,4-dihydroquinoline-3-carboxylic acid (mmol) in dry dichloromethane (10 ml) bromotrimethylsilane (1.3 ml, 10 mmol) was added and the mixture was reacted for three days at room temperature. It was then evaporated to dryness and water (10 ml) was added to the residue. It was stirred for one day and evaporated. Dichloromethane (10 ml) was added, and it was stirred overnight. The product was then recovered by filtration and dried in vacuum to yield 0.42 g (62.7%). M.p. 205° C.

$^1$H-NMR: δ (D20) 8.48 (1H, s, H-2); 7.53 (1H, d, H-5); 7.0 (1H, d, H-8); 4.35 (2H, q, $CH_3CH_2N$); 3.6 (10H, m, piperidine+$NCH_2CH$); 2.5 (1H, m, CHP); 1.5 (3H, t, $CH_3CH_2N$).

Anal.: Cal.c'd. for $C_{18}H_{24}FN_3O9P_2 \cdot 2HBr$ (669.36) C, 32.29; H, 3.91; N, 6.28; P, 9.26

Found: C, 32.42; H, 4.24; N, 6.13; P, 9.47.

What is claimed is:

1. A compound of the formula

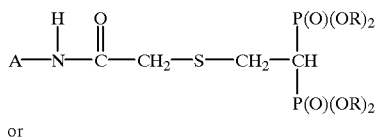

or

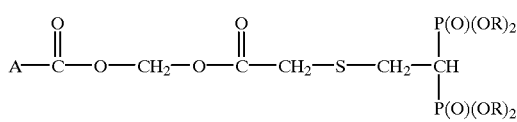

wherein R is H or an aliphatic group of from 1 to 10 carbon atoms and A is an organic group.

2. A compound of claim 1 wherein A is the residue of a pharmaceutically active compound.

3. A compound of the formula A—X—Z wherein A is the residue of a pharmaceutically active compound, X is a linking group that is cleavable in vivo or in vitro by esterase and Z is

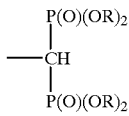

wherein R is H or alkyl of from 1 to 10 carbons.

4. A compound of claim 3 wherein the linking group

X is 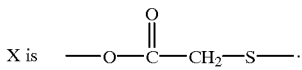

5. A method of preparing a compound of claim 1 comprising reacting a compound of the formula $ANH_2$ or $A—COOCH_2Cl$ where A is an organic group with a 2,2-bis-(dialkoxy-substituted-phosphoryl)-ethyl-sulfanyl-acetic acid wherein each dialkoxy group contains from 1 to 10 carbon atoms.

6. A method of preparing a compound of claim 2 comprising reacting a compound of the formula $ANH_2$ or $A—COOCH_2Cl$ where A is the residue of a pharmaceutically active compound with a 2,2-bis-(di-substituted-phosphoryl)-ethyl-sulfanyl-acetic acid wherein each phosphoryl group substituent contains from 1 to 10 carbon atoms.

7. A compound of claim 1 that is cleavable by esterase.

8. A compound of claim 2 that is cleavable by esterase.

9. A method of releasing the residue A in a compound of claim 1 in vitro comprising treating the compound with esterase.

10. A method of releasing the residue A in a compound of claim 2 in vitro comprising treating the compound with esterase.

11. A method of releasing the residue A in a compound of claim 1 in vivo comprising administering the compound to an organism containing esterase.

12. A method of releasing the residue A in a compound of claim 2 in vivo comprising administering the compound to an organism containing esterase.

13. A compound of claim 3 wherein the enzyme is esterase and the linking group X is

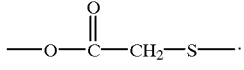

* * * * *